US006756389B2

(12) United States Patent
Durant et al.

(10) Patent No.: US 6,756,389 B2
(45) Date of Patent: Jun. 29, 2004

(54) PHARMACEUTICALLY ACTIVE COMPOUNDS AND METHODS OF USE

(75) Inventors: Graham J. Durant, Wellesley Hills, MA (US); Michael Maillard, Cambridge, MA (US); Jun Qing Guo, Waltham, MA (US)

(73) Assignee: Cambridge Neuroscience, Inc., Cambridge, MA (US)

( * ) Notice: Subject to any disclaimer, the term of this patent is extended or adjusted under 35 U.S.C. 154(b) by 0 days.

(21) Appl. No.: 08/694,906

(22) Filed: Aug. 9, 1996

(65) Prior Publication Data

US 2003/0069274 A1 Apr. 10, 2003

(51) Int. Cl.⁷ ..................... A61K 31/445; C07D 211/06
(52) U.S. Cl. ...................... 514/331; 546/231; 546/215
(58) Field of Search .................... 514/331; 546/231, 546/215, 246

(56) References Cited

U.S. PATENT DOCUMENTS

| | | | |
|---|---|---|---|
| 2,633,474 A | 3/1953 | Beaver ..................... 260/565 |
| 2,704,710 A | 3/1955 | Sprung ........................ 95/2 |
| 3,119,831 A | 1/1964 | Homer ..................... 260/296 |
| 3,121,645 A | 2/1964 | Bindler et al. ........... 117/138.5 |
| 3,122,555 A | 2/1964 | Janssen .................. 260/292.4 |
| 3,140,231 A | 7/1964 | Luskin et al. ................ 167/65 |
| 3,159,676 A | 12/1964 | Spickett et al. ............. 260/564 |
| 3,168,562 A | 2/1965 | Walton et al. .............. 260/564 |
| 3,200,151 A | 8/1965 | Spickett et al. ............. 260/564 |
| 3,228,975 A | 1/1966 | Abraham et al. ........... 260/501 |
| 3,248,426 A | 4/1966 | Dvornil ..................... 260/564 |
| 3,252,861 A | 5/1966 | Mull .......................... 167/65 |
| 3,256,278 A | 6/1966 | Petracek ................. 260/247.5 |
| 3,270,054 A | 8/1966 | Gagneux et al. ............ 260/564 |
| 3,283,003 A | 11/1966 | Jack et al. .................. 260/564 |
| 3,284,289 A | 11/1966 | Duerr et al. ................. 167/30 |
| 3,301,755 A | 1/1967 | Mull .......................... 167/65 |
| 3,305,552 A | 2/1967 | Cragoe, Jr. et al. ......... 260/250 |
| 3,320,229 A | 5/1967 | Szabo et al. ............... 260/96.5 |
| 3,403,156 A | 9/1968 | Humber et al. ............. 260/286 |
| 3,409,669 A | 11/1968 | Dyke ........................ 260/564 |
| 3,479,437 A | 11/1969 | Szabo et al. ................ 424/304 |
| 3,527,871 A | 9/1970 | Engelhardt et al. ......... 424/330 |
| 3,547,951 A | 12/1970 | Hardie et al. ............ 260/340.9 |
| 3,597,433 A | 8/1971 | Dobson et al. ......... 260/286 R |
| 3,624,259 A | 11/1971 | Galantay ................. 260/479 R |
| 3,639,477 A | 2/1972 | L'Italien ................. 260/564 A |
| 3,678,109 A | 7/1972 | Knowles ................. 260/564 R |
| 3,681,459 A | 8/1972 | Hughes et al. .............. 260/565 |
| 3,689,675 A | 9/1972 | Knowles ..................... 424/326 |
| 3,723,463 A | 3/1973 | Yale et al. ............... 260/327 B |
| 3,804,898 A | 4/1974 | Panneman .............. 260/564 A |
| 3,812,119 A | 5/1974 | Walker ...................... 260/247 |
| 3,822,262 A | 7/1974 | Bream et al. ......... 260/256.4 H |
| 3,888,927 A | 6/1975 | Hamakawa et al. .... 260/564 R |
| 3,903,163 A | 9/1975 | McCathy, Jr. ........... 260/564 R |
| 3,906,044 A | 9/1975 | Algami et al. .......... 260/564 R |
| 3,908,013 A | 9/1975 | Hughes et al. .............. 424/258 |
| 3,914,306 A | 10/1975 | Douglas et al. ......... 260/562 R |
| 3,949,089 A | 4/1976 | Maxwell et al. ............ 424/326 |
| 3,965,176 A | 6/1976 | Gold .................... 260/564 RF |
| 3,968,211 A | 7/1976 | DuCharme ................. 424/248 |
| 3,972,931 A | 8/1976 | McCarthy, Jr. .......... 260/564 R |
| 3,975,533 A | 8/1976 | Kodama et al. ............ 424/326 |
| 3,976,643 A | 8/1976 | Diamond et al. ..... 260/247.5 R |
| 3,976,787 A | 8/1976 | Hughes et al. .............. 424/326 |
| 3,983,250 A | 9/1976 | Abdallah et al. ........... 424/326 |
| 3,987,158 A | 10/1976 | Hodson ........................ 424/9 |
| 3,988,474 A | 10/1976 | Abdallah et al. ........... 424/326 |
| 4,014,934 A | 3/1977 | Hughes et al. .............. 260/565 |
| 4,051,256 A | 9/1977 | Swallow ..................... 424/304 |
| 4,052,455 A | 10/1977 | Matier et al. ........... 260/562 R |
| 4,052,508 A | 10/1977 | Anderson et al. ........... 424/258 |
| 4,060,640 A | 11/1977 | Kodama et al. ............ 424/326 |
| 4,064,139 A | 12/1977 | Anderson et al. ........ 260/313.1 |
| 4,093,655 A | 6/1978 | Miller et al. .......... 260/564 RF |

(List continued on next page.)

FOREIGN PATENT DOCUMENTS

| | | |
|---|---|---|
| CA | 1081711 | 7/1980 |
| DE | 3108564 | 11/1982 |
| EP | 0 035 374 | 9/1981 |
| EP | 0 179 642 | 4/1986 |
| EP | 0 235 942 | 9/1987 |
| EP | 0 266 574 | 5/1988 |
| EP | 0 296 560 | 12/1988 |
| EP | 0 372 934 | 6/1990 |
| EP | 0 501 552 | 9/1992 |
| GB | 966493 | 8/1964 |
| GB | 2244486 | * 12/1991 |
| WO | WO 90/14067 | 11/1990 |
| WO | WO 92/19621 | 11/1992 |
| WO | WO 93/00313 | 1/1993 |
| WO | WO 94/22807 | 10/1994 |
| WO | WO 94/27591 | 12/1994 |
| WO | WO 95/00131 | 1/1995 |
| WO | WO 95/14461 | 6/1995 |
| WO | WO 95/14467 | 6/1995 |
| WO | WO 95/20950 | 8/1995 |
| ZA | 92/0990 | 11/1992 |
| ZA | 92/0944 | 10/1993 |
| ZA | 94/9253 | 3/1996 |

OTHER PUBLICATIONS

Seyfried, T.N.: Audiogenic seizures in mice. Fed. Proceed. vol. 38, pp. 2399–2404, 1979.*

Reddy, N.L. et al.: Synthesis and structure–activity studies of diarylguanidine derivatives, J. Med. Chem. vol. 37, pp. 260–267, 1994.*

Primary Examiner—Charanjit S. Aulakh
(74) Attorney, Agent, or Firm—Edwards & Angell, LLP; Jeffery D. Hsi

(57) ABSTRACT

The present invention relates to certain imine-substituted heterocyclic compounds, and methods of treatment and pharmaceutical compositions that utilize or comprise one or more such compounds. Compounds of the invention are particularly useful for the treatment or prophylaxis of neurological injury and neurodegenerative disorders.

26 Claims, No Drawings

U.S. PATENT DOCUMENTS

| | | | |
|---|---|---|---|
| 4,109,014 A | 8/1978 | Liu et al. | 424/326 |
| 4,130,663 A | 12/1978 | Matier et al. | 424/326 |
| 4,134,992 A | 1/1979 | Abdallah et al. | 424/326 |
| 4,154,947 A | 5/1979 | Goldman et al. | 542/417 |
| 4,161,541 A | 7/1979 | Rasmussen | 424/326 |
| 4,198,417 A * | 4/1980 | Ong et al. | 424/267 |
| 4,284,642 A | 8/1981 | Toldy et al. | 424/273 R |
| 4,318,915 A | 3/1982 | Cohnen et al. | 424/273 R |
| 4,332,822 A | 6/1982 | Ward | 424/324 |
| 4,342,765 A | 8/1982 | Jones et al. | 424/249 |
| 4,353,912 A | 10/1982 | Neumeyer | 424/258 |
| 4,369,325 A | 1/1983 | Toldy et al. | 548/315 |
| 4,374,836 A | 2/1983 | Yellin et al. | 424/251 |
| 4,374,838 A | 2/1983 | Anderson et al. | 424/256 |
| 4,379,160 A | 4/1983 | Harfenist et al. | 424/274 |
| 4,393,077 A | 7/1983 | Douglas et al. | 424/326 |
| 4,400,383 A | 8/1983 | Davidson et al. | 424/250 |
| 4,433,152 A * | 2/1984 | Muramatsu et al. | |
| 4,465,677 A | 8/1984 | DeMarinis et al. | 424/244 |
| 4,470,989 A | 9/1984 | Henning et al. | 424/267 |
| 4,471,137 A | 9/1984 | Barton et al. | 564/240 |
| 4,575,514 A | 3/1986 | Carson | 514/542 |
| 4,649,222 A | 3/1987 | Georgiev et al. | 564/459 |
| 4,680,300 A | 7/1987 | Nelson et al. | 514/312 |
| 4,709,094 A | 11/1987 | Weber et al. | 564/238 |
| 4,742,054 A | 5/1988 | Naftchi | 514/215 |
| 4,778,812 A | 10/1988 | Jirkovsky | 514/323 |
| 4,780,466 A | 10/1988 | Hrib et al. | 514/254 |
| 4,789,673 A | 12/1988 | Donatsch et al. | 514/214 |
| 4,833,138 A | 5/1989 | Olney | 514/226.2 |
| 4,837,218 A | 6/1989 | Olney | 514/646 |
| 4,863,953 A | 9/1989 | Leeson et al. | 514/425 |
| 4,866,062 A | 9/1989 | Toth et al. | 514/255 |
| 4,866,076 A | 9/1989 | Gribble | 514/307 |
| 4,873,262 A | 10/1989 | Junge et al. | 514/510 |
| 4,888,347 A | 12/1989 | Woodruff et al. | 514/289 |
| 4,898,978 A | 2/1990 | Bergfeld et al. | 564/231 |
| 4,906,779 A | 3/1990 | Weber et al. | 564/238 |
| 4,918,064 A | 4/1990 | Cordi et al. | 514/114 |
| 4,940,789 A | 7/1990 | Childers, Jr. et al. | 540/581 |
| 4,945,097 A | 7/1990 | Olney | 514/318 |
| 4,962,107 A | 10/1990 | Nakamura et al. | 514/237.5 |
| 4,962,115 A | 10/1990 | Van Daele | 514/326 |
| 5,011,834 A | 4/1991 | Weber et al. | 514/212 |
| 5,089,634 A | 2/1992 | Powers et al. | 549/285 |
| 5,093,525 A | 3/1992 | Weber et al. | 564/238 |
| 5,190,976 A * | 3/1993 | Weber et al. | 514/634 |
| 5,262,568 A | 11/1993 | Weber et al. | 564/238 |
| 5,308,869 A | 5/1994 | Keana et al. | 514/637 |
| 5,312,840 A | 5/1994 | Keana et al. | 514/634 |
| 5,336,689 A | 8/1994 | Weber et al. | 514/634 |
| 5,364,871 A * | 11/1994 | Takasugi et al. | 514/342 |
| 5,385,946 A | 1/1995 | Keana et al. | 514/634 |
| 5,403,861 A | 4/1995 | Goldin et al. | 514/634 |
| 5,478,863 A | 12/1995 | Keana et al. | 514/634 |
| 5,502,255 A | 3/1996 | Keana et al. | 564/230 |
| 5,552,443 A | 9/1996 | Keana et al. | 514/631 |
| 6,143,791 A * | 11/2000 | Goldin et al. | 514/634 |

* cited by examiner

PHARMACEUTICALLY ACTIVE COMPOUNDS AND METHODS OF USE

BACKGROUND OF THE INVENTION

1. Field of the Invention

The present invention relates to certain imine-substituted heterocyclic compounds, and methods of treatment and pharmaceutical compositions that utilize or comprise one or more such compounds. Compounds of the invention are particularly useful for the treatment or prophylaxis of neurological injury and neurodegenerative disorders.

2. Background

Nerve cell death (degeneration) can cause potentially devastating and irreversible effects for an individual and may occur e.g. as a result of stroke, heart attack or other brain or spinal chord ischemia or trauma. Additionally, neurodegenerative disorders involve nerve cell death (degeneration) such as Alzheimer's disease, Parkinson's disease, Huntington's disease, Amyotrophic Lateral Sclerosis, Down's Syndrome and Korsakoff's disease.

Therapies have been investigated to treat nerve cell degeneration and related disorders, e.g., by limiting the extent of nerve cell death that may otherwise occur to an individual. See, e.g., N. L. Reddy et al., *J. Med. Chem.*, 37:260–267 (1994); and WO 95/20950.

The compound MK-801 has exhibited good results in a variety of in vivo models of stroke. See B. Meldrum, *Cerbrovascular Brain Metab. Rev.*, 2:27–57 (1990); D. Choi, *Cerbrovascular Brain Metab. Rev.*, 2:105–147 (1990). See also Merck Index, monograph 3392, 11th ed., 1989. For example, MK-801 exhibits good activity in mouse audiogenic tests, a recognized model for evaluation of neuroprotective drugs. See, e.g., M. Tricklebank et al., *European Journal of Pharmacology*, 167:127–135 (1989); T. Seyfried, *Federation Proceedings*, 38(10):2399–2404 (1979).

However, MK-801 also has shown toxicity and further clinical development of the compound is currently uncertain. See J. W. Olney et al., *Science*, 244:1360–1362 (1989); W. Koek et al., *J. Pharmacol. Exp. Ther.*, 252:349–357 (1990); F. R. Sharp et al., *Society for Neuroscience Abstr.*, abstr. no. 482.3 (1992).

It thus would be highly desirable to have new neuroprotective agents, particularly agents to limit the extent or otherwise treat nerve cell death (degeneration) such as may occur with stroke, heart attack or brain or spinal cord trauma, or to treat neurodegenerative disorders such as Alzheimer's disease, Parkinson's disease, Huntington's disease, Amyotrophic Lateral Sclerosis, Down's Syndrome and Korsakoff's disease.

SUMMARY OF THE INVENTION

In a first aspect, the present invention provides imine-substituted compounds of the following Formula I:

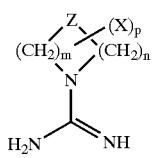

I wherein Z is sulfur, oxygen, carbon or nitrogen;

m and n are each independently an integer from 0 to 4, and the sum of m and n is at least 2, preferably is 3, 4, 5 or 6, more preferably 3, 4 or 5;

each X is independently substituted or unsubstituted alkyl preferably having from 1 to about 20 carbon atoms; substituted or unsubstituted alkylsilyl preferably having 1 to about 20 carbon atoms and 1 or more Si atoms; substituted or unsubstituted alkenyl preferably having from 2 to about 20 carbon atoms; substituted or unsubstituted alkynyl preferably having from 2 to about 20 carbon atoms; substituted or unsubstituted alkoxy preferably having from 1 to about 20 carbon atoms, including haloalkoxy; substituted or unsubstituted alkylthio preferably having from 1 to about 20 carbon atoms; substituted or unsubstituted alkylamino preferably having from 1 to about 20 carbon atoms; substituted or unsubstituted alkylsulfinyl preferably having 1 to about 20 carbon atoms; substituted or unsubstituted alkylsulfonyl preferably having 1 to about 20 carbon atoms; substituted or unsubstituted carbocyclic aryl preferably having at least about 6 ring carbon atoms; substituted or unsubstituted aralkyl preferably having from 7 to about 18 carbons; or a substituted or unsubstituted heteroaromatic or heteroalicyclic group having from 1 to 3 rings, 3 to 8 ring members in each ring and from 1 to 3 hetero atoms;

p is an integer equal to 0 (where the ring is substituted only by the depicted —C(=NH)NH$_2$ substituent) to 14, more typically from 0 to about 4; and pharmaceutically acceptable salts thereof.

Substituted or unsubstituted methylene (—CH$_2$—) is a generally preferred Z ring member. Generally preferred X groups include substituted and unsubstituted alkyl, substituted and unsubstituted alkylsilyl, substituted and unsubstituted alkenyl, substituted and unsubstited alkynyl, substituted and unsubstituted alkylthio, substituted and unsubstituted alkylamino, substituted and unsubstituted alkylsulfinyl, substituted and unsubstituted alkylsulfonyl, substituted and unsubstituted aralkyl, substituted and unsubstituted carbocyclic aryl, and substituted and unsubstituted heteroaromatic or heteroalicyclic groups.

Particularly preferred X groups included substituted and unsubstituted alkyl and substituted and unsubstituted carbocyclic aryl, particularly substituted and unsubstituted naphthyl or phenyl such as naphthyl or phenyl substituted by alkyl or haloalkyl having 1 to about 6 carbons, halogen, alkylthio, particularly alkylthio having 1 to about 6 carbon atoms such as methylthio and ethylthio, and alkylsilyl preferably having 1 to about 15 carbon atoms.

It is understood that the imine-substituted ring nitrogen shown in the above formula generally would not be substituted by an X group. It is further understood that the ring methylene (CH$_2$) groups (which include Z where Z is carbon) of the above Formula I will include only a single hydrogen if the methylene unit is mono-substituted by an X group, i.e. the methylene unit will be (CHX), or the methylene unit will contain no hydrogens if di-substituted by X groups, i.e. the methylene unit will be (CXX). It is also understood the range of p values will depend in part on the sum of m and n as well as the valence of the Z ring substituent. Thus, for example, if the sum of m and n is 4 and without limitation on the Z ring member, p will be an integer of from 0 to 10, but if Z is specified to be oxygen, then p will be an integer of from 0 to 8, or if Z is nitrogen then p will be an integer of from 0 to 10.

Generally preferred compounds of Formula I include six-member ring compounds (i.e. where the sum of m and n above is four), particularly compounds of the following Formula Ia:

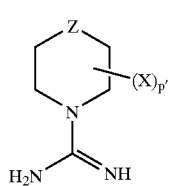

Ia wherein Z and X are each the same as defined above for Formula I; p' is an integer of from 0 (where the ring is substituted only by the —C(=NH)NH$_2$ substituent) to 10, more typically from 0 to about 4; and pharmaceutically acceptable salts thereof.

Particularly preferred compounds of Formula I are substituted piperidines of the following Formula Ib:

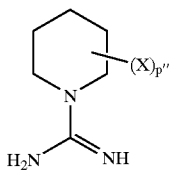

Ib wherein X is the same as defined above for Formula I; p" is an integer of from 0 (where the ring is substituted only by the depicted imine) to 10, more typically from 0 to about 4; and pharmaceutically acceptable salts thereof.

Preferred compounds of the invention have at least two ring substituents (p≧2 in Formula I), particularly 2,6-substituted compounds of Formula Ia, such as the following substituted piperidine compounds of Formula Ic:

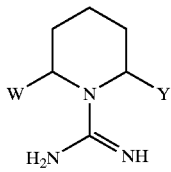

Ic wherein W and Y are each independently substituted or unsubstituted alkyl preferably having from 1 to about 20 carbon atoms; substituted or unsubstituted alkylsilyl preferably having 1 to about 20 carbon atoms and 1 or more Si atoms; substituted or unsubstituted alkenyl preferably having from 2 to about 20 carbon atoms; substituted or unsubstituted alkynyl preferably having from 2 to about 20 carbon atoms; substituted or unsubstituted alkoxy preferably having from 1 to about 20 carbon atoms, including haloalkoxy; substituted or unsubstituted alkylthio preferably having from 1 to about 20 carbon atoms; substituted or unsubstituted aminoalkyl preferably having from 1 to about 20 carbon atoms; substituted or unsubstituted alkylsulfinyl preferably having 1 to about 20 carbon atoms; substituted or unsubstituted alkylsulfonyl preferably having 1 to about 20 carbon atoms; substituted or unsubstituted carbocyclic aryl preferably having at least about 6 ring carbon atoms; substituted or unsubstituted aralkyl preferably having from 7 to about 18 carbon atoms; or a substituted or unsubstituted heteroaromatic or heteroalicyclic group having from 1 to 3 rings, 3 to 8 ring members in each ring and from 1 to 3 hetero atoms; and pharmaceutically acceptable salts thereof.

Generally preferred W and Y groups include substituted and unsubstituted alkyl, substituted and unsubstituted alkylsilyl, substituted and unsubstituted alkenyl, substituted and unsubstituted alkynyl, substituted and unsubstituted alkylthio, substituted and unsubstituted alkylamino, substituted and unsubstituted alkylsulfinyl, substituted and unsubstituted alkylsulfonyl, substituted and unsubstituted aralkyl, substituted and unsubstituted carbocyclic aryl, and substituted and unsubstituted heteroaromatic or heteroalicyclic groups.

Particularly preferred W and Y groups included substituted and unsubstituted alkyl and substituted and unsubstituted carbocyclic aryl, particularly substituted and unsubstituted naphthyl or phenyl such as naphthyl or phenyl substituted by alkyl or haloalkyl having 1 to about 6 carbons, halogen, alkylthio, particularly alkylthio having 1 to about 6 carbon atoms such as methylthio, and alkylsilyl preferably having 1 to about 15 carbon atoms.

In a second aspect, imine-substituted compounds are provided that are substituted by a group other than hydrogen on the imine or adjacent non-cyclic nitrogen. Preferred are compounds of the following Formula II:

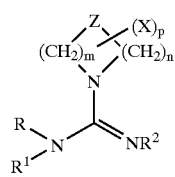

II wherein Z, X, p, m and n are the same as defined above for Formula I; R, R$^1$ and R$^2$ are each independently hydrogen; hydroxy; substituted or unsubstituted alkanoyl having from 1 to about 20 carbon atoms; substituted or unsubstituted alkanoyloxy having from 1 to about 20 carbon atoms; substituted or unsubstituted alkyl preferably having from 1 to about 20 carbon atoms; substituted or unsubstituted alkenyl preferably having from 2 to about 20 carbon atoms; substituted or unsubstituted alkynyl preferably having from 2 to about 20 carbon atoms; substituted or unsubstituted alkoxy preferably having from 1 to about 20 carbon atoms; substituted or unsubstituted alkylthio preferably having from 1 to about 20 carbon atoms; substituted or unsubstituted alkylamino preferably having from 1 to about 20 carbon atoms; substituted or unsubstituted alkylsulfinyl preferably having 1 to about 20 carbon atoms; substituted or unsubstituted alkylsulfonyl preferably having 1 to about 20 carbon atoms; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 hetero atoms, with at least one of R, R$^1$ and R$^2$ being other than hydrogen; and pharmaceutically acceptable salts thereof.

Preferred compounds of Formula II include six-member ring compounds (sum of m and n above is four), particularly compounds of the following Formula IIa:

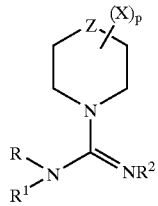

IIa wherein Z and X are each the same as defined above for Formula I; p is an integer of from 0 to 10, more typically 0 to about 4; R, $R^1$ and $R^2$ are each the same as defined above for Formula II; and pharmaceutically acceptable salts thereof. Substituted piperidine compounds are generally preferred, i.e. where Z is carbon.

Also preferred are compounds of Formula II that have at least two ring substituents (p>2 in Formula II), particularly 2,6-substituted compounds of Formula IIa, such as the following piperidine compounds of Formula IIb:

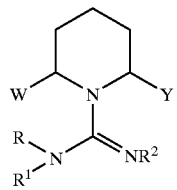

IIb wherein W and Y are the same as defined above for Formula Ic; R, $R^1$ and $R^2$ are each the same as defined above for Formula II; and pharmaceutically acceptable salts thereof.

Generally preferred X, W and Y groups of compounds of Formula II, IIa and IIb include substituted and unsubstituted alkyl, substituted and unsubstituted alkylsilyl, substituted and unsubstituted alkenyl, substituted and unsubstituted alkynyl, substituted and unsubstituted alkylthio, substituted and unsubstituted alkylamino, substituted and unsubstituted alkylsulfinyl, substituted and unsubstituted alkylsulfonyl, substituted and unsubstituted aralkyl, substituted and unsubstituted carbocyclic aryl, and substituted and unsubstituted heteroaromatic or heteroalicyclic groups.

Particularly preferred X, W and Y groups of compounds of Formula II, Ia and IIb include substituted and unsubstituted alkyl and substituted and unsubstituted carbocyclic aryl, particularly substituted or unsubstituted naphthyl or phenyl such as naphthyl or phenyl substituted by alkyl or haloalkyl having 1 to about 6 carbons, halogen, alkylthio, particularly alkylthio having 1 to about 6 carbon atoms such as methylthio or ethylthio, and alkylsilyl preferably having 1 to about 15 carbon atoms.

Preferred R and $R^1$ groups of compounds of Formulae II, IIa and IIb include substituted and unsubstituted carbocyclic aryl and heteroaromatic and heteroalicyclic groups. Particularly preferred R and $R^1$ groups are substituted and unsubstituted naphthyl and phenyl groups, such as naphthyl or phenyl substituted at one or more ring positions by alkyl or haloalkyl having 1 to about 6 carbons, halogen, alkylthio, particularly alkylthio having 1 to about 6 carbon atoms such as methylthio. Other preferred R and $R^1$ groups include hydroxy, alkyl, alkenyl, alkynyl, alkoxy, alkylthio, alkylamino, alkylsulfinyl, alkylsulfonyl, substituted or unsubstituted alkanoyl and substituted or unsubstituted alkanoyloxy. Generally preferred are compounds of Formulae II, IIa and IIb are those where at least one of R and $R^1$ is other than hydrogen, and $R^2$ is hydrogen.

As with compounds of Formula I, it is understood with respect to the compounds of Formula II that the depicted imine-substituted ring nitrogen would not be substituted by an X group. It is further understood that the ring methylene groups ($CH_2$) of the above Formula II will include only a single hydrogen if the methylene unit is mono-substituted by an X group, i.e. the methylene unit will be (CHX), or the methylene unit will contain no hydrogens if di-substituted by X groups, i.e. the methylene unit will be (CXX). It is also understood the range of p values will depend in part on the sum of m and n as well as the valence of the Z ring substituent.

The invention also includes both racemic mixtures and optically enriched mixtures of chiral compounds of the invention. An optically enriched mixture contains substantially more (e.g. about 60%, 70%, 80% or 90% or more) of one enantiomer or diastereoisomer than the other stereoisomer(s). Preferred optically enriched mixtures contain 97% or more, more preferably 98% or more, even more preferably 99% or more of one enantiomer or diastereoisomer than the other stereoisomer(s).

Compounds of the invention are useful for a number of therapeutic applications. In particular, the invention includes methods for treatment and/or prophylaxis of neurological conditions/injuries such as epilepsy, neurodegenerative conditions and/or nerve cell death (degeneration) resulting from e.g. hypoxia, hypoglycemia, brain or spinal chord ischemia, retinal ischemia, brain or spinal chord trauma or post-surgical neurological deficits and the like as well as neuropathic pain. The compounds of the invention are especially useful for treatment of a person susceptible or suffering from stroke or heart attack or neurological deficits relating to cardiac arrest, a person suffering or susceptible to brain or spinal cord injury, or a person suffering from the effects of retinal ischemia or degeneration. Compounds of the invention also are useful to treat and/or prevent various neurodegenerative diseases such as Parkinson's disease, Huntington's disease, Amyotrophic Lateral Sclerosis, Alzheimer's disease, Down's Syndrome, Korsakoff's disease, cerebral palsy and/or age-dependent dementia. Compounds of the invention will be further useful to treat and/or prevent migraines, shingles (herpes zoster), epilepsy, emesis and/or narcotic withdrawal symptoms. Also, in addition to treatment of retinal ischemia and related disorders, the invention provides methods for treatment of optic nerve injury/damage. The treatment methods of the invention in general comprise administration of a therapeutically effective amount of one or more compounds of the invention to an animal, including a mammal, particularly a human.

Particularly preferred compounds of the invention exhibit good activity in an anticonvulsant in vivo mouse audiogenic assay e.g. as disclosed in Example 6 which follows, preferably about 20% or more inhibition at a dose of a compound of the invention of 20 mg/kg, more preferably about 50% or more or 70% or more inhibition at a dose of 20 mg/kg in such an anticonvulsant in vivo audiogenic assay.

The invention also provides pharmaceutical compositions that comprise one or more compounds of the invention and a suitable carrier for the compositions.

The invention further provides methods for preparation of compounds of the invention as well as amine (particularly compounds of Formula III below), N-cyano and other compounds useful as intermediates in those preparative methods. Other aspects of the invention are disclosed infra.

DETAILED DESCRIPTION OF THE INVENTION

The present invention provides imine-substituted compounds of the following Formulae I and II:

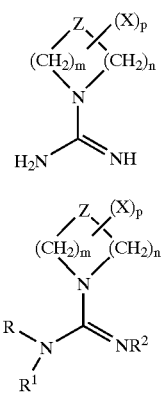

wherein Z, X, p, m, n, R, $R^1$ and $R^2$ are as defined above; and pharmaceutically acceptable salts of those compounds.

Suitable halogen substituent groups of compounds of Formulae I, Ia, Ib, Ic, II, IIa and IIb as defined above (i.e. compounds of the invention) include F, Cl, Br and I. Alkyl groups of compounds of the invention preferably have from 1 to about 12 carbon atoms, more preferably 1 to about 8 carbon atoms, still more preferably 1 to about 6 carbon atoms, even more preferably 1, 2, 3 or 4 carbon atoms. Methyl, ethyl and propyl including isopropyl are particularly preferred alkyl groups of compounds of the invention. As used herein, the term alkyl unless otherwise modified refers to both cyclic and noncyclic groups, although of course cyclic groups will comprise at least three carbon ring members. Preferred alkylsilyl groups include alkylsilyl having 1 to about 15–18 carbons and 1 or about 2 Si atoms, e.g. a trialkylsilyl group such as a trimethylsilyl, triethylsilyl, a butyl(dimethyl)silyl or tributylsilyl group. Preferred alkenyl and alkynyl groups of compounds of the invention have one or more unsaturated linkages and from 2 to about 12 carbon atoms, more preferably 2 to about 8 carbon atoms, still more preferably 2 to about 6 carbon atoms, even more preferably 2, 3 or 4 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1 to about 6 carbon atoms, even more preferably 1, 2, 3 or 4 carbon atoms. Preferred substituted alkoxy groups include haloalkoxy such as fluoroalkoxy, e.g. trifluoromethoxy, trifluroethoxy, pentafluoroethoxy and the like. Preferred alkylthio groups of compounds of the invention include those groups having one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred. Preferred alkylsulfinyl groups of compounds of the invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred. Preferred alkylamino groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties. Preferred alkanoyl groups have from 1 to about 8 carbons and one or two carbonyl groups, with acetyl ($CH_3CO$) and acyl being preferred. Alkanoyloxy groups preferably contain one, two or more oxygen linkages, one or two carbonyl groups and and from 1 to about 8 carbons. Preferred groups include $C_{1-8}C(=O)O-$. Suitable heteroaromatic substituent groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic substituent groups of compounds of the invention contain one or more N, O or S atoms and include, e.g., tetrahydrofuranyl, tetrahydropyranyl, piperidinyl, morpholino and pyrrolindinyl groups. Suitable carbocyclic aryl groups of compounds of the invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl, such as 2-substituted phenyl, 3-substituted phenyl, 4-substituted phenyl or 2,3-substituted, 2,4-substituted phenyl, including where such phenyl substituents are selected from the same group as defined above in Formula I for the substituent X; naphthyl including 1-naphthyl and 2-naphthyl; biphenyl; phenanthryl; and anthracyl. As mentioned above, substituted and unsubstituted carbocyclic aryl, particularly substituted and unsubstituted naphthyl and phenyl, are preferred X, W and Y groups of compounds of the invention. Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and $-CH_2$-naphthyl.

References herein to substituted X, W, Y, R, $R^1$ and $R^2$ groups of compounds of the invention refer to the specified moiety that may be substituted at one or more available positions by one or more suitable groups such as, e.g., halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkylsilyl groups such as those groups having from 1 to about 12 carbons, or more preferably 1 to about 6 carbons and 1 or Si groups; alkoxy groups including those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; alkylamino groups such as groups having one or more N atoms and from 1 to about 12 carbon atoms or from 1 to about 6 carbon atoms; carbocyclic aryl having 6 or more carbons, particularly phenyl; and aralkyl having from about 7 to 14 carbon atoms such as benzyl; and heteroaromatic or heteroalicyclic group having from 1 to 3 rings, 3 to 8 ring members in each ring and from 1 to 3 hetero atoms.

It should be understood that alkoxy, alkylthio, alkylsulfinyl, alkylsulfonyl and aminoalkyl substituent groups described above include groups where a hetero atom is directly bonded to a ring system, such as a carbocyclic aryl group or a heterocyclic group, as well as groups where a hetero atom of the group is spaced from such ring system by an alkylene linkage, e.g. of 1 to about 4 carbon atoms.

Specifically preferred compounds of the invention include the following:
N-carboximidamide-r-2, c-6-di(4-methylphenyl)piperidine;
N-carboximidamide-r-2, c-6-di(4-isopropylphenyl) piperidine;
N-carboximidamide-r-2, t-6-di(4-methylphenyl)piperidine;
N-carboximidamide-r-2, c-6-diphenylpyrrolidine;
N-(N'-phenyl)carboximidamide-r-2, c-6-diphenylpiperidine;
and pharmaceutically acceptable salts thereof. See General of Organic Chemistry, vol. 56, 4833–4840 (1991) for discussion of the nomenclature of these preferred compounds. The structural formulae of these preferred compounds are also shown in the examples which follow.

Compounds of the invention can be prepared by several routes. For example, compounds of the invention can be prepared by reaction of cyanamide with a precursor derivative of Formula I that does not contain the N-substituent of —C(=NH)NH$_2$ or —C(=NR$^2$)NRR$^1$, i.e. a compound of the following Formula III (where Z, X, m, n and p are each the same as defined above for Formula I):

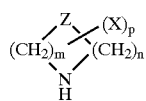

III

More particularly, compounds of the invention can be suitably prepared by reaction of a precursor compound of Formula III above with cyanamide to provide compounds of Formula I, or a substituted cyanamide to provide compounds of Formula II, in a suitable solvent such as methanol, ethanol and chloroform or the like under an inert atmosphere such as argon or nitrogen. Typically, an HCl or other acid addition salt of the precursor compound III is reacted with the cyanamide. The reaction solution is suitably heated e.g. from about 100° C. or greater for 2 to about 60 hours until reaction completion, e.g. as indicated by thin layer chromatography. The reaction solution is then cooled to room temperature, and the solvent is then removed under reduced pressure to provide the desired compound of the invention. The crude product then can be purified by recrystallization and/or column chromatography, e.g. by elution one or more times on silica gel (e.g., 60–200 mesh, 50×w/w) with suitable solvents. See Example 1, Part II which follows for exemplary conditions.

Precursor compounds of the above Formula III may be commercially available or can be prepared by reduction of the corresponding unsaturated heterocyclic nitrogen compound, e.g. by use of a reducing agent such as sodium and ethanol. See Example 1, Part 1 for exemplary conditions of such reduction. Hydrogenation also may be employed using palladium or other suitable catalyst. See Example 4, Part III. The nitrogen may be suitably activated during hydrogenation, e.g. with an oxycarbonyl group such as t-butoxycarbonyl or the like, which group can be then removed such as by acidic hydrolysis prior to reaction with cyanamide or other reagent. See Example 4 which follows for an exemplary procedure.

Substituted unsaturated cyclic amine compounds to employ in such reduction reactions can be prepared by several methods. For example, an organometallic reagent can be prepared (typically Group I or II metal, particularly Li or Mg) such as by a halogen-metal exchange reaction followed by reaction of that organometallic reagent with a halopyridine or other halogen-substituted cyclic amine. See Example 2, Part 1, Method A for an exemplary procedure.

Alternatively, a substituted pyridine or other unsaturated precursor compound can be prepared by cyclization of an intermediate compound that contains the ring substituents (i.e. groups X, W and Y in the above formulae), e.g. by cyclization of a substituted 1,5-diketopentyl compound with hydroxylamine. See Example 2, Method B which follows for exemplary conditions.

Compounds of Formulae I and II also may be prepared by reaction of a precursor compound of Formula III above with cyanogen bromide to provide the N-cyano derivative (i.e. compounds of Formula III above substituted at the depicted ring nitrogen by cyano). That cyano intermediate then may be suitably reacted an amine, particularly an ammonium salt such as an acetate salt, typically with heating to provide the N-imine substituted compound of Formula I. See Example 3 which follows for exemplary conditions. Compounds of Formula II may be prepared by reaction of the N-cyano derivative with a primary or secondary amine (to provide the desired R and R$^1$ groups as defined above for Formula II) in the presence of a Lewis acid such as AlCl$_3$ and the like. See Example 5 which follows for an exemplary synthesis.

Alkylsulfinyl-substituted or alkylsulfonyl-substituted reagents, that can provide correspondingly substituted compounds of the invention as described above, can be provided by oxidation (e.g., H$_2$O$_2$) of alkylthio-substituted reagents.

As discussed above, chiral compounds of the invention may be used as optically enriched or racemic mixtures. An optically enriched mixture contains substantially more (e.g. about 60%, 70%, 80% or 90% or more) of one enantiomer or diastereoisomer than the other stereoisomer(s). Optically enriched mixtures can be obtained by known procedures, e.g., column chromatography using an optically active binding material or formation of a salt using an optically active material, particularly an optically active acid.

As discussed above, the present invention includes methods for treating or preventing certain neurological disorders, including the consequences of stroke, heart attack and traumatic head or brain injury, epilepsy or neurodegenerative diseases comprising the administration of an effective amount of one or more compounds of the invention to a subject including a mammal, particularly a human, in need of such treatment. In particular, the invention provides methods for treatment and/or prophylaxis of nerve cell death (degeneration) resulting e.g. from hypoxia, hypoglycemia, brain or spinal cord ischemia, brain or spinal cord trauma, stroke, heart attack or drowning. Typical candidates for treatment include e.g. heart attack, stroke and/or persons suffering from cardiac arrest neurological deficits, brain or spinal cord injury patients, patients undergoing major surgery such as heart surgery where brain ischemia is a potential complication and patients such as divers suffering from decompression sickness due to gas emboli in the blood stream. Candidates for treatment also will include those patients undergoing a surgical procedure involving extracorporal circulation such as e.g. a bypass procedure.

The invention in particular provides methods for treatment which comprise administration of one or more compounds of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurism or hemorrhage. Thus, an effective amount of one or more compounds of the present invention could be administered pre-operatively or peri-operatively to reduce such risks associated with carotid endarterectomy, or other post-surgical neurological deficits.

The invention further includes methods for prophylaxis against neurological deficits resulting from e.g. coronary artery bypass graft surgery and aortic valve replacement surgery, or other procedure involving extra-corporal circulation. Those methods will comprise administering to a patient undergoing such surgical procedures an effective amount of one or more compounds of the invention, typically either pre-operatively or peri-operatively.

The invention also provides methods for prophylaxis and treatment against neurological injury for patients undergoing myocardial infarction, a procedure that can result in ischemic insult to the patient. Such methods will comprise administering to a patient undergoing such surgical procedure an effective amount of one or more compounds of the invention, typically either pre-operatively or peri-operatively.

Also provided are methods for treating or preventing neuropathic pain such as may experienced by cancer patients, persons having diabetes, amputees and other persons who may experience neuropathic pain. These methods for treatment comprise administration of an effective amount of one or more compounds of the invention to a patient in need of such treatment.

The invention also provides methods for treatment and prophylaxis against eye disorders and injury, including methods for treatment of reduced flow of blood or other nutrients to retinal tissue or optic nerve, methods for treatment of retinal ischemia and trauma and associated disorders, and methods for treatment of optic nerve damage/injury. Disorders associated with retinal or optic nerve injury or ischemia that may be treated in accordance with the invention include e.g. diabetes, significantly elevated intraocular pressures and glaucoma, diseases such as retinal artery or vein occlusion, atherosclerosis, venous capillary insufficiency, senile macular degeneration and cystoid macular edema. In such methods, a compound of the invention can be administered parenterally or by other procedure as described herein to a subject a suffering from or suscep-tible to ischemic insult or other injury or disorder that may adversely affect visual function. Post-ischemic or post-injury administration also may limit retinal damage. Intra-vitreal injection of a compound of the invention also may be a preferred administration route to provide more direct treatment to the injured retina or optic nerve.

The invention also provides methods for treatment of a subject suffering from shingles as well as treatment of a person suffering from or susceptible to migraines, particularly to alleviate the pain and discomfort associated with those disorders. These methods comprise administration of an effective amount of one or more compounds of the invention to a patient in need of treatment.

The invention further provides a method of treating Korsakoff's disease, a chronic alcoholism-induced condition, comprising administering to a subject including a mammal, particularly a human, one or more compounds of the invention in an amount effective to treat the disease. Compounds of the invention are anticipated to have utility for the attenuation of cell loss, hemorrhages and/or amino acid changes associated with Korsakoff's disease.

As discussed above, the invention also includes methods for treating a person suffering from or susceptible to cerebral palsy, emesis, narcotic withdrawal symptoms and age-dependent dementia, comprising administering to a subject including a mammal, particularly a human, one or more compounds of the invention in an amount effective to treat the condition.

As discussed above, preferred compounds of the invention are active in a standard anticonvulsant in vivo audiogenic test, such as the audiogenic mouse assay of Example 6 which follows, where DBA/2 mice about 20–23 days old are injected intraperitoneally with a test compound 30 minutes prior to being placed in a bell jar with exposure to auditory stimulus of 12 KHz sine wave at 110–120 db. References herein in vivo "audiogenic assay" are intended to refer to that protocol. Generally preferred compounds exhibit 20% or more inhibition (relative to subjects treated with vehicle control only) at a dose of 20 mg/kg, more preferably about 50% or more or 70% or more inhibition at a dose of 20 mg/kg in such an in vivo audiogenic assay. As discussed above, activity in the audiogenic assay has been recognized as indicative that a test compound has neuroprotective properties. See, e.g., M. Tricklebank et al., *European Journal of Pharmacology*, supra; T. Seyfried, *Federation Proceedings*, supra.

The invention also provides methods for determining binding activity of compounds of the invention as well as in vitro and in vivo binding activity diagnostic methods using one or more radiolabelled compounds of the invention, e.g., a compound of the invention that is labeled with $^{125}$I, tritium, $^{32}$P, $^{99}$Tc, or the like, preferably $^{125}$I. For instance, a compound of the invention having a phenyl or other aryl substituent that is ring substituted with one or more $^{125}$I groups can be administered to a mammal and the subject then scanned for binding of the compound. Specifically, single photon emission computed tomography ("SPECT") can be employed to detect such binding. Such an analysis of the mammal could e.g. aid in the diagnosis and treatment of acute cerebral ischemia. That is, a labeled compound of the invention will selectively bind to ischemic tissue of e.g. a subject's brain to differentiate between ischemic and non-ischemic tissue and thereby assess trauma or other injury to the brain.

Accordingly, the invention includes compounds of the invention that contain a radiolabel such as $^{125}$I, tritium, $^{32}$P, $^{99}$Tc, or the like, preferably 125I1. Such radiolabelled compounds can be suitably prepared by procedures known in the synthesis art. For example, a compound of the invention having an aromatic group, such as phenyl, that has a bromo or chloro ring substituent can be employed in an exchange labeling reaction to provide the corresponding compound having an $^{125}$I ring substituent.

Compounds of the invention may be used in therapy in conjunction with other medicaments. For example, for treatment of a stroke victim or a person susceptible to stroke, one or more compounds of the invention may be suitably administered together with a pharmaceutical targeted for interaction in the blood clotting mechanism such as streptokinase, tPA, urokinase and other agents that lyse clots. Also, one or more compounds of the invention may be administered together with agents such as heparin and related heparin-based compounds, acenocoumarol or other known anticoagulants.

Compounds of the invention also may function as prodrugs and may be metabolized in vivo to forms of enhanced activity.

The compounds of this invention can be administered intranasally, orally or by injection, e.g., intramuscular, intraperitoneal, subcutaneous or intravenous injection, or by transdermal, intraocular or enteral means. The optimal dose can be determined by conventional means. Compounds of the present invention are suitably administered to a subject in the protonated and water-soluble form, e.g., as a pharmaceutically acceptable salt of an organic or inorganic acid, e.g., hydrochloride, sulfate, hemisulfate, phosphate, nitrate, acetate, oxalate, citrate, maleate, mesylate, etc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are preferred. The compounds of this invention are particularly valuable in the treatment of mammalian subjects, e.g., humans, to provide neuroprotective therapy and/or prophylaxis. Typically, such subjects include those afflicted with neurodegenerative diseases such as Parkinson's disease, Huntington's disease, Amyotrophic Lateral Sclerosis, Alzheimer's disease, Down's Syndrome and Korsakoff's disease. Also suitable for treatment are those subjects suffering from or likely to suffer from nervous system dysfunctions resulting from, for example, epilepsy or nerve cell degeneration which is the result of hypoxia, hypoglycemia, brain or spinal chord ischemia or brain or spinal chord trauma. As discussed above, typical candidates for treatment include heart attack, stroke, brain or spinal cord injury patients, patients undergoing major surgery where brain or spinal cord ischemia is a potential complication and patients such as divers suffering from decompression sickness due to gas emboli in the blood stream.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of the invention particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage, preferably from 0.2 to 2 milligrams per unit dosage.

Compounds of the invention also can be useful as rubber accelerators. See U.S. Pat. No. 1,411,713 for a discussion of rubber accelerator applications.

The entire text of all documents cited herein are incorporated by reference herein. The following non-limiting examples are illustrative of the invention.

General Comments

In the following examples, all percentages reported herein, unless otherwise specified, are percent by weight. All temperatures are expressed in degrees Celsius.

Melting points were determined in open capillary tubes on a Thomas-Hoover apparatus and are uncorrected. Thin-layer chromatography was performed on Baker-flex 1B2-F silica gel plates. Compounds were visualized on TLC with 254-nM UV light or as a blue spot with bromcresol spray reagent (Sigma Chemical Co.). Preparative TLC was performed on Analtech GF precoated silica gel (1000 $\mu$m) glass-backed plates (20×20 cm). NMR spectra were recorded on Varian Gemini 300 and the chemical shifts were reported in ppm ($\delta$) relative to the residual signal of the deuterated solvent ($CDCl_3$, $\delta7.26$; $CHD_2OD$, $\delta3.30$). Elemental analyses were performed by either Galbraith Laboratories (Knoxville, Tenn.) or MHW Laboratories (Tuscon, Ariz.). High Resolution Mass spectra (HRMS) were recorded on a Finnegan MAT 90. HPLC were performed on a C18 reverse phase column using 50:50 water:acetonitrile with 0.1% TFA as a mobile phase. Chlorobenzene, ether (Et$_2$O) and tetrahydrofuran (THF) were anhydrous quality solvents (Sure Seal) supplied by Aldrich. All other solvents were reagent grade.

EXAMPLE 1

Preparation of N-carboximidamide-r-2, c-6-di(4-methylphenyl)piperidine, Mesylate (Includes Parts I and II)

Part I: Preparation of r-2, c-6-di(4-methylphenyl)piperidine, Hydrochloride and (+)r-2,t-6-di(4-methylphenyl)piperidine, Hydrochloride

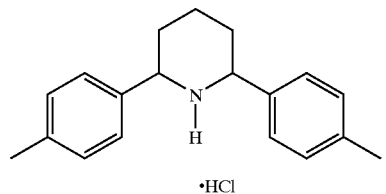

•HCl

To a solution of 2,6-di-p-tolylpyridine (3.0 g, 11.6 mmol) in 30 ml of absolute ethanol was added sodium (6.0 g, 0.26 mol) in small pieces and the reaction was kept at gentle reflux. After the addition of sodium was completed, 10 ml of ethanol was added and the reaction mixture was heated to reflux until the sodium had disappeared. The solution was cooled to room temperature and 50 ml of water were added dropwise. Ethanol was evaporated from the reaction mixture, the aqueous phase was extracted several times with diethyl ether and the combined etherates were washed with water, brine and dried over MgSO$_4$. The drying agent was removed by filtration and the etherate was concentrated to yield a crude product which was purified on silica gel column with hexane/ethyl acetate as eluant (20/1 to 10/1) to afford r-2, c-6-di(4-methylphenyl)piperidine and r-2, t-6-di (4-methylphenyl)piperidine. To form the HCl salt, r-2, c-6-di(4-methylphenyl)piperidine was dissolved in a minimum amount of diethyl ether and 5 ml of 1N HCl (5 mmol) diethyl ether solution was added. The precipitate was collected by filtration, washed with diethyl ether and dried to afford r-2, c-6-di(4-methylphenyl)piperidine, HCl (1.35 g, 38.7%). r-2, c-6-Di(4-methylphenyl)piperidine was converted to the HCl salt by the same method as r-2, c-6-di(4-methylphenyl) piperidine to afford r-2, t-6-di(4-methylphenyl)piperidine, HCl (1.28 g, 33.8%). r-2, c-6-Di(4-methylphenyl)piperidine, HCl: a white solid; purity 95.9% (HPLC); Mass: 265(m/c); mp:315–317° C.; TLC: R$_f$=0.32 (hexane/ethylacetate 10/1); $^1$H-NMR (CD$_3$OD):δppm 7.42 (d, ArH, 4H) 7.26 (d, ArH, 4H), 4.42 (t, ArCH, 2H), 2.35 (s, CH$_3$, 6H), 1.85–2.20 (m, CH$_2$, 6H); Anal. (C, H, N; C$_{19}$H$_{23}$N, HCl): cal. (%):C, 75.60; H, 8.01; N, 8.01; found(%): C, 75.43; H, 8.05; N, 4.65. r-2,t-6-Di(4-methylphenyl)piperidine, HCl: a white solid purity 98.2% (HPLC); Mass: 265 (m/e); mp: 279–281° C.; TLC: R$_f$=0.15 (hexane/ethylacelate 10/1); $^1$H-NMR (CD$_3$OD): δppm 7.39 (d, ArH, 4H), 7.32 (d, ArH, 4H), 4.54 (t, ArCH, 2H), 2.38 (s, CH$_3$, 6H), 1.90–2.40 (m, CH$_2$,6H);

Anal. (C, H, N: C$_{19}$H$_{23}$N, HCl): cal.(%): C, 75.60; H, 8.01; N, 4.64; found (%): C, 75.82; H, 7.85; N, 4.8.

Part II: Preparation of N-carboximidamide-r-2, c-6-di(4-methyphenyl)piperidine, Mesylate

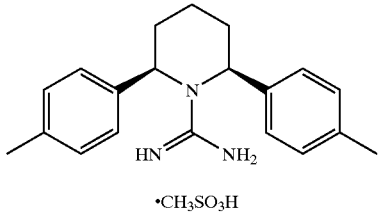

•CH$_3$SO$_3$H

Cyanamide (1.50 g, 35.7 mmol) and r-2, c-6-di(4-methylphenyl)piperidine hydrochloride (0.50 g, 1.66 mmol) were dissolved in 20 ml of methanol and the reaction mixture was refluxed for 48 hours. The solution was concentrated to afford a crude product which was purified on silica gel column with chloroform/methanol (20/1) as eluant. The product was collected, concentrated and dissolved in 100 ml of 1N NaOH. The solution was extracted with chloroform, the organic phase was washed with 1N NaOH, water, brine and dried over MgSO$_4$. After filtration and evaporation to dryness, the light-yellow solid obtained was dissolved in diethyl ether. To this solution was added sulfonic acid (70 mg, 0.72 mmol). The precipitate obtained was collected by filtration, washed with diethyl ether and dried under vacuum (0.256 g, 48.2%). A white solid; purity: 86.4% (HPLC); HRMS: 307.2048 (Cal.:307.2033 for C$_{20}$H$_{25}$N$_3$); mp: 183–185° C.; TLC: R$_f$=0.43 (SiO$_2$, CHCl$_3$/MeOH=10/1). $^1$H-NMR (CD$_3$OD): δ ppm 7.25 (d, ArH, 4H), 7.15 (d, ArH, 4H), 4.93 (t, ArCH, 2H), 2.69 (s, CH$_3$SO$_3$H, 3H), 2.30 (s, CH$_3$, 6H), 1.80–2.30 (m, CH$_2$,6H).

EXAMPLE 2

Preparation of N-carboximidamide-r-2,c-6-di(4-isopropylphenyl)piperidine, Hydrochloride (Includes Parts 1, II and III; Part I Carried Out with Alternative Methods A and B)

Part I: Preparation of 2,6-di(4-isopropylphenyl)pyridine

Method A

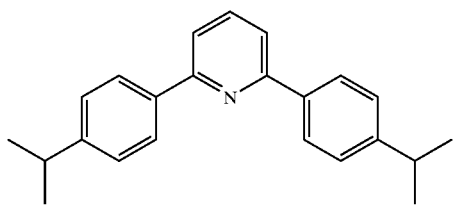

To a solution of 4-bromoisopropylbenzene (3.0 g, 14.8 mmol) in 10 ml of diethyl ether was added dropwise under argon, at −78° C., n-butyllithium 2.5M in hexanes (5.91 ml, 14.8 mmol) and then the reaction mixture was warmed to −10 to 0° C. 2,6-Difluoropyridine (0.858 g, 7.39 mmol) was added dropwise over one hour period. After stirring for 30 minutes, the reaction mixture was warmed up to room temperature and stirred for 16 hours. The reaction was quenched with a 20% ammonium chloride solution, the organic phase was separated and the aqueous phase was extracted with diethyl ether. The combined etherates were dried over MgSO$_4$, and filtration and concentration afforded a crude product which was purified on silica gel column with chloroform as eluant. The product was collected, concentrated and dried to yield the title compound (0.87 g, 37.4%). $^1$H-HMR(CDCl$_3$); δ ppm 8.08 (d, ArH, 4H), 7.80 (t, ArH, 1H), 7.65 (d, ArH, 2H), 7.36 (d, ArH, 4H), 3.00 (m, CH, 2H), 1.30(d, CH$_3$, J=6.93 Hz, 12H).

Method B

Part 1: Preparation of 1,3,-di(4'-isopropylbenzoyl) propane

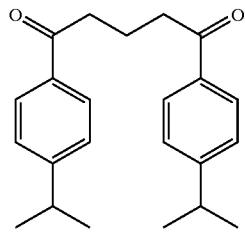

To a solution of cumene (5.00 g, 41.2 mmol) in methylene chloride (80 ml) was added AlCl$_3$ (5.49 g, 41.2 mmol) under argon at 0 to 5° C. Glutaryl chloride (3.58 g, 20.0 mmol) in methylene chloride (30 ml) was added and the mixture was warmed to room temperature and stirred for 12 hours. The reaction was then poured into 100 ml of ice water and the organic phase separated. The aqueous phase was extracted several times with chloroform. The combined organic phases were washed with water, NaOH 1N, brine and dried over MgSO$_4$. Filtration and evaporation to dryness afforded a crude product which was purified on silica gel column with chloroform. The product was collected, concentrated and dried (4.55 g, 68%). $^1$H-NMR (CDCl$_3$): δ ppm 7.92 (d, ArH, 4H), 7.31 (d, ArH, 4H), 3.09 (t, CH$_2$, J=7.0 Hz, 4H), 2.98 (m, CH, 2H), 2.19 (m, CH$_2$, 2H), 1.26 (d, CH$_3$, J=6.93, 12H).

Part 2: Preparation of 2,6-di(4-isopropylphenyl)pyridine

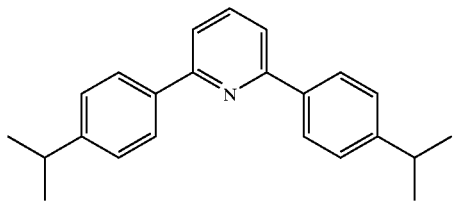

1,3-Di(4'-isopropylbenzoyl) propane (1.85 g, 5.50 mmol) and hydroxylamine hydrochloride (0.414 g, 5.89 mmol) were dissolved in glacial acetic acid (7 ml). After 24 hours of reflux, the reaction mixture was cooled down to room temperature and concentrated to afford a brown oil to which was added 100 ml of water. To this solution was added 1N NaOH until pH=13. The aqueous phase was extracted several times with chloroform. The combined organic phases were washed with 1N NaOH, water, brine and dried over MgSO$_4$. Filtration and evaporation to dryness afforded a crude product which was purified on silica gel column with hexane/ethyl acetate (20:1) as eluant. The product was collected, concentrated and dried (0.521 g, 30%). $^1$H-NMR (CDCl$_3$) for the product corresponded to that set forth above under Example 2 Part I, Method A.

Part II: Preparation of r-2, c-6-di(4-isopropylphenyl) piperidine, Hydrochloride

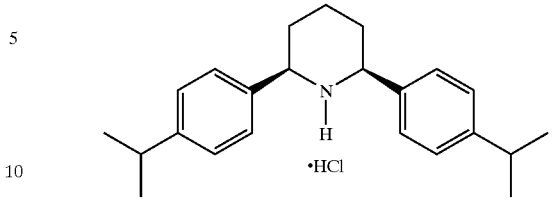

This compound was prepared by the method set forth in Example 1, Part 1 above with use of 2,6-di(4-isopropylphenyl)pyridine) in place of 2,6-di-p-tolylpyridine. $^1$H-NMR(CD$_3$OD): δ ppm 7.49 (d, ArH, 4H), 7.35 (d, ArH, 4H), 4.45 (t, ArCH, 2H), 2.92 (m, CH, 2H), 2.15 (m, CH$_2$, 6H), 1.35(d, CH$_3$, J=6.93 Hz, 12H).

Part III: Preparation of N-carboximidamide-r-2, c-6-di(4-isopropylphenyl)piperidine, Hydrochloride

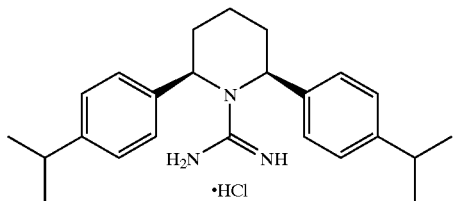

This compound was prepared by the method set forth in Example I Part II above with use of r-2, c-6-di(4-isopropylphenyl)piperidine, hydrochloride in place of r-2, c-6-di(4-methylphenyl)piperidine. r-2,c-6-Di(4-isopropylphenyl)piperidine, HCl: a white solid; purity 99.7% (HPLC); Mass: 364 MH$^+$; mp: 197–199° C.; TLC: R$_f$=0.29 (SiO$_2$,CHCl$_3$/MeOH=10/1); $^1$H-NMR (CD$_3$OD): δppm 7.27 (d, ArH, 4H), 7.18 (d, ArH, 4H), 4.97 (m, ArCH, 2H), 2.85 (m, CH, 2H), 1.80–2.30 (m, CH$_2$, 6H), 1.21 (d, CH$_3$ J=6.93 Hz, 12H); Anal. (C,H,N; C$_{24}$H$_{33}$N$_3$, HCl): cal.(%): C, 72.06; H, 8.57; N, 10.50; found (%): C, 72.18; H, 8.49; N, 10.59.

EXAMPLE 3

Preparation of (⇋) N-carboximidamide-r-2, t-6-di(4-methylphenyl) piperidine, Hydrochloride (Parts I, II and III)

Part I: Preparation of (+)2,6-di(4-methylphenyl)piperidine

This compound was prepared by the method indicated above in Example 1, Part 1 and omitting the HCl treatment.

Part II: Preparation of (+)N-cyano-r-2,t-6-di(4-methylphenyl)piperidine

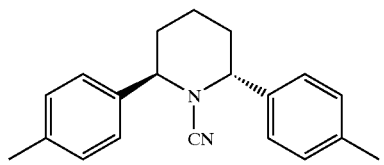

(+)r-2, t-6-(4-Methyl)phenylpiperidine (365 mg, 1.37 mmol) was suspended in 30 ml of an ice-bath cooled mixture of methanol-water 2:1. Ammonium acetate (170 mg, 2.05 mmol) and cyanogen bromide (220 mg, 2.05 mmol) were added successively. After two hours of stirring, the water bath was removed and the suspension stirred overnight. The white flaky precipitate obtained was collected on a glass filter and washed with water: yield 215 mg (54%); $^1$H-NMR (CDCl$_3$): δ ppm 7.34 (d, ArH, 4H), 7.23 (d, ArH, 4H), 4.48 (dd, ArCH, J=4.3, 7.0 Hz, 2H), 2.36 (s, CH$_3$, 6H), 2.20 (m, CH$_2$, 2H), 2.05 (m, CH$_2$, 2H), 1.78 (m, CH$_2$, 2H); purity 89% (HPLC); TLC: R$_f$=0.3 (hexane-ethylacetate 2/0.5); Mass (CI—NH$_3$): 308 (M+NH$_4$)$^+$, 291(MH)$^+$.

Part III:

Preparation of (+) N-Carboximidamide-r-2, t-6-di(4-methylphenyl)piperidine, Hydrochloride

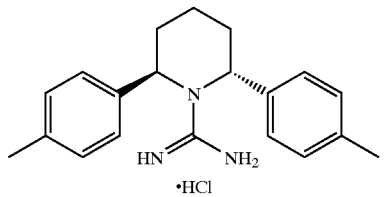

(+) N-cyano-r-2, t-6(4-methyl)phenylpiperidine (215 mg, 0.75 mmol) was mixed with an excess of ammonium acetate (1.5 g) and the paste obtained was heated to the melting point at 120° C. to obtain a clear solution. After 13 hours of heating, the solution was cooled down and water was added. This solution was kept in the freezer until precipitation occurred (12 hours). The precipitate was filtered off and the filtrate basified with sodium hydroxide 1N. The filtrate was extracted with diethyl-ether, washed with water and acidified with HCl 1N to precipitate (+) N-carboximidamide-r-2, t-6-di(4-methylphenyl) piperidine, HCl as a white solid: yield 60 mg (28%), $^1$H-NMR (CD$_3$OD): δ ppm 7.4 (d, ArH, 4H), 7.3 (d, ArH, 4H), 4.55 (dd, 2ArCH, 2H), 2.4 (s, CH$_3$, 6H), 2.35 (m, CH$_2$, 2H), 2.15 (m, CH$_2$, 2H), 1.95 (m, CH$_2$, 2H), Mass: MH$^+$(308), MH—CN$_2$H$_2$ (266); purity: 98.9% (HPLC); TLC: R$_f$=0.3 (chloroform/methanol 10/0.5).

EXAMPLE 4

Preparation of N-carboximidamide-r-2,c-6-diphenylpyrrolidine, Hydrochloride (Includes Parts I, II, III, IV and V)

Part I: Preparation of 2,6-diphenylpyrrole

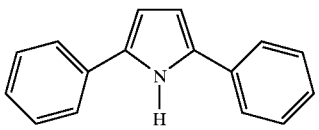

Dibenzoylethane (1.50 g, 6.30 mmol) and ammonium acetate (2.00 g, 25.2 mmol) were mixed together and the mixture was heated to 100° C. for 4 hours. The reaction mixture was cooled down to room temperature, diluted with 30 ml of water and basified with 1N NaOH until pH 14. The reaction mixture was extracted several times with chloroform. The combined organic phases were washed with 1N NaOH, water, brine and dried over MgSO$_4$. Filtration and concentration afforded a crude product which was purified on silica gel column with hexanes/ethyl acetate (10/1) as eluant, the product was collected to yield after evaporation to dryness 0.90 g (65.2%). A light yellow solid; $^1$H-NMR (CDCl$_3$): δ ppm 7.20–7.60 (m, ArH, 10H), 6.6 (d, ArH, 2H).

Part II: Preparation of N-Boc-2-6-diphenylpyrrole

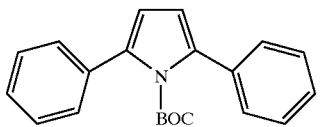

4-Dimethylaminopyridine (DMAP) (5.4 mg, 0.046 mmol) and di-tert-butyldicarbonate (100 mg. 0.456 mmol) were added to a solution of 2,6-diphenylpyrrole (100 mg, 0.456 mmol) in dry acetonitrile (5 ml) under argon. The reaction mixture was refluxed for 5 hours. The crude product was purified on silica gel column with hexanes/ethyl acetate (10/1) as eluant. The product was collected, concentrated and dried to afford the title compound, N-t-butyloxycarbonyl-2,6-diphenylpyrrole as an oil (126 mg, 86.6%). $^1$H-NMR (CDCl$_3$): δ ppm 7.25–7.55 (m, ArH, 10H), 6.6 (d, ArH, 2H), 1.17 (s, CH$_3$, 9H).

Part III: Preparation of N-Boc-2-6-diphenylpyrrolidine

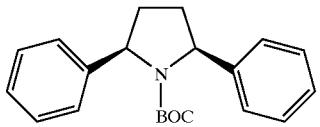

To a solution of N-Boc-2,6-diphenylpyrrole (1.027 g, 3.22 mmol) in methanol (80 ml) was added palladium (5%) on activated carbon (0.250 g). The reaction mixture was hydrogenated (10 psi) for 1.5 hours. Filtration and evaporation to dryness afforded N-Boc-2,6-diphenylpyrrolidine (1.01 g, 97%). $^1$H-NMR (CDCl$_3$): δ ppm 7.20–7.60 (m, ArH, 10H), 5.0 (m, ArCH, 2H), 2.45 (m, CH$_2$, 2H), 1.17 (s, CH$_3$, 9H).

Part IV: Preparation of 2,6-diphenylpyrrolidine, Hydrochloride

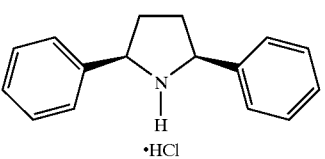

Trifluoroacetic acid (10 ml) was added to 2,6-diphenylpyrrolidine (1.01 g, 3.13 mmol) at 0° C. The mixture was stirred at 0° C. for 10 minutes, then the solvent was evaporated to afford a light brown solid to which was added 100 ml of water. To this solution was added 1N NaOH until pH=14 and the aqueous phase was extracted with chloroform. The organic phase was washed with 1N NaOH, water, brine and dried over MgSO$_4$. After filtration and evaporation to dryness, the light-yellow solid obtained was dissolved in diethyl-ether. To this solution was added 1N HCl (5 ml, 5 mmol), the precipitate obtained was collected by filtration, washed with diethyl-ether and dried under vacuum (0.590 g, 72.7%). $^1$N-NMR (CDCl$_3$): δ ppm 7.30–7.60 (m, ArH, 10H), 4.95 (m,ArCH,2H), 2.45–2.70 (m, CH$_2$, 4H).

Part V: Preparation of N-carboximidamide-r-2, c-6-diphenylpyrrolidine Hydrochloride

Cyanamide (1.40 g. 33.3 mmol) and r-2, c-6-diphenylpyrrolidine (0.50 g, 1.92 mmol) were dissolved in 10 ml of methanol. The reaction mixture was refluxed for 24 hours. The solution was concentrated to afford a crude product which was purified on silica gel column with chloroform/methanol (24/1). The products were collected, concentrated and dissolved in 100 ml of 1N NaOH. The solution was extracted with chloroform. The organic phase was washed with 1N NaOH, water, brine and dried over $MgSO_4$. Filtration and evaporation to dryness gave a fluffy solid which was dissolved in 3 ml of chloroform. To this solution was added 3 ml of 1N HCl in diethyl ether (3 mmol). The precipitate was collected by filtration and washed with diethyl ether and dried under vacuum (0.210 g, 36.2%); a white solid; purity: 99.5% (HPLC); Mass: 266 $MH^+$; mp: 242–244° C.; TLC: $R_f$=0.23 ($SiO_2$ $CHCl_3$/MeOH=10/1); $^1$H-NMR ($CD_3OD$): δ ppm 7.45–7.55 (m, ArH, 10H), 5.17 (t, ArCH, 2H), 2.58 (m, $CH_2$,2H), 2.10 (m, $CH_2$, 2H); Anal. (C, H, N; $C_{17}H_{19}N_3$, HCl, 0.7$H_2O$): cal. (%): C, 64.97; H, 6.81; N, 13.38; found (%): C, 64.59; H, 6.39; N, 13.43.

EXAMPLE 5

Preparation of N—(N'-phenylcarboximidamide)-r-2,c-6-diphenylpiperidine, Hydrochloride (Includes Parts I, II and III)

Part I: Preparation of 2,6-diphenylpiperidine, Hydrochloride

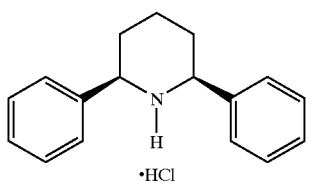

This compound was prepared as described in Example 1, Part I. $^1$H-NMR ($CDCl_3$): δ ppm 7.20–7.50 (m, ArH, 10H), 3.82 (d, ArCH, 2H), 1.45–2.05 (m, $CH_2$,6H).

Part II: Preparation of N-cyano-r-2, c-6-diphenylpiperidine

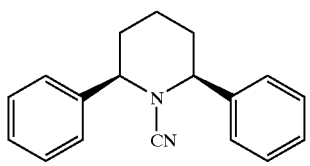

This compound was prepared as described in Example 3, Part II above. $^1$H-NMR ($CDCl_3$): δ ppm 7.30–7.50 (m, ArH, 10H), 4.18(d, ArCH, 2H), 1.60–2.10(m, $CH_2$, 6H).

Part III: Preparation of N-(N'-phenylcarboximidamide)-r-2, c-6-diphenyl Piperidine, Hydrochloride

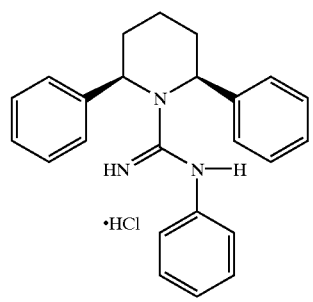

To a solution of N-cyano-r-2-6-diphenylpiperidine (200 mg. 0,76 mmol) in chlorobenzene (5 ml) was added $AlCl_3$ (100 mg, 0.76 mmol) and the suspension was stirred for 5 minutes. Aniline hydrochloride (100 mg, 0.76 mmol) was added, and the reaction mixture was heated to 120° C. for 4 hours. The reaction mixture was purified on silica gel column with chloroform/methanol (20/1). The fractions containing the product were evaporated to dryness to yield 0.127 g (42.5%). A white fluffy solid; purity 92.3% (HPLC); Mass: 356 $MH^+$; mp: 82–84° C.; TLC: $R_f$=0.37 ($SiO_2$, $CHCl_3$/MeOH=20/1); $^1$H-NMR ($CD_3OD$): δ ppm 7.10–7.50 (m, ArH, 15H), 4.76 (t, ArCH, J=7.26 Hz, 2H), 2.00–2.40 (m, $CH_2$, 6H); Anal. (C, H, N; $C_{24}H_{25}N_3$, HCl): cal. (%): C, 73.55; H, 6.69; N, 10.72; found (%) C, 73.63; H, 6.52; N, 10.88.

EXAMPLE 6

In vivo Anticonvulsant activity in the DBA/2 Mouse Model (Mouse Audiogenic Assay)

The in vivo potency of compounds of the invention is exemplified by data summarized in the Table I below and obtained pursuant to the following protocol.

Compounds were tested for their effectiveness in preventing seizures in DBA/2 mice which have a unique sensitivity to auditory stimulation. Exposure to loud high-frequency sounds can trigger seizure activity in these animals. This sensitivity develops from postnatal day 12 and peaks around day 21 and slowly diminishes as the animals mature. The unusual response to auditory stimulation in this strain of mouse is believed to be due to a combination of early myelination (causing an unusually low excitatory threshold) and delayed development of inhibitory mechanisms.

Mice were injected intraperitoneally with the compound specified in Table I below or with vehicle control, 30 minutes prior to being placed in a bell jar and turning on the auditory stimulus (12 KHz sine wave at 110–120 db). Administered doses are specified in Table I as milligram of compound per kilogram bodyweight of mouse. The auditory stimulus was left on for 60 seconds and mice reactions were timed and recorded. Percentage inhibition was determined with reference to vehicle controls. Results are shown in Table I below.

TABLE I

| Example No. | Compound Name | Audiogenic Response | | Salt |
|---|---|---|---|---|
| | | Dose (mg/kg) | % Inhib. | |
| 1 | N-carboximidamide-r-2, c-6-di(4-methylphenyl)piperidine | 10 | 42 | mesylate |
| 2 | N-carboximidamide-r-2, c-6-di(4-isopropylphenyl)piperidine | 10 | 69 | HCl |

This invention has been described in detail with reference to preferred embodiments thereof. However, it will be appreciated that those skilled in the art, upon consideration of this disclosure, may make modifications and improvements within the spirit and scope of the invention.

What is claimed is:

1. A compound of the following formula:

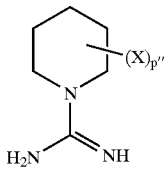

wherein X is independently unsubstituted alkyl; substituted or unsubstituted alkenyl; substituted or unsubstituted alkynyl; substituted or unsubstituted alkoxy; substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms;

p" is an integer of from 0 to 10; and pharmaceutically acceptable salts thereof.

2. A compound of the following formula:

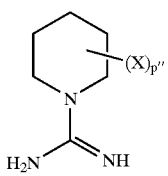

wherein X is independently substituted or unsubstituted alkyl; substituted or unsubstituted alkenyl; substituted or unsubstituted alkynyl; substituted or unsubstituted alkoxy; substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms, wherein substituted X groups may be substituted by one or more halogen; cyano; hydroxyl; nitro; azido; alkanoyl; carboxamido; alkyl; alkenyl; alkynyl; alkylsilyl, alkoxy groups; aryloxy; alkylthio; alkylsulfinyl; alkylsulfonyl; alkylamino; carbocyclic aryl; aralkyl; and heteroaromatic or heteroalicyclic group having from 1 to 3 rings, 3 to 8 ring members in each ring and from 1 to 3 N, O or 5;

p" is an integer of from 0 to 10; and pharmaceutically acceptable salts thereof.

3. A compound of the following formula:

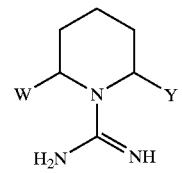

wherein W and Y are each independently substituted or unsubstituted alkyl; substituted or unsubstituted alkenyl; substituted or unsubstituted alkynyl; substituted or unsubstituted alkoxy; substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms; and pharmaceutically acceptable salts thereof.

4. A compound of claim 1 that is

N-carboximidamide-r-2, c-6-di(4-methylphenyl)piperidine;

N-carboximidamide-r-2, c-6-di(4-isopropylphenyl)piperidine; or

N-carboximidamide-r-2, t-6-di(4-methylphenyl)piperidine;

or a pharmaceutically acceptable salt thereof.

5. A compound of the following formula:

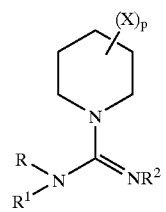

wherein each X is independently substituted or unsubstituted alkyl; substituted or unsubstituted alkenyl; substituted or unsubstituted alkynyl; substituted or unsubstituted alkoxy; substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms;

R is hydrogen; hydroxy; substituted or unsubstituted alkanoyl; substituted or unsubstituted alkanoyloxy; unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms;

R1 and R2 are each independently hydrogen; hydroxy; substituted or unsubstituted alkanoyl; substituted or unsubstituted alkanoyloxy; substituted or unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms, with at least one of R, $R^1$ and $R^2$ being other than hydrogen;

p is an integer of from 0 to 10; and pharmaceutically acceptable salts thereof, with the exclusion of N-N'-naphthylcarboximide-piperidine, N-N'-naphthylcarboximide-(4phenyl)piperidine; and N-N' (meta-ethylphenyl)carboximide(4phenyl)piperidine.

6. A compound of the following formula:

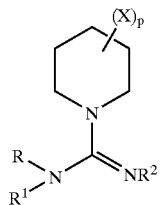

wherein each X is independently substituted or unsubstituted alkyl; substituted or unsubstituted alkenyl; substituted or unsubstituted alkynyl; substituted or unsubstituted alkoxy, substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms;

R is hydrogen; hydroxy; substituted or unsubstituted alkanoyl; substituted or unsubstituted alkanoyloxy; substituted or unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms, wherein substituted R groups may be substituted by one or more halogen; cyano; hydroxyl; nitro; azido; alkanoyl; carboxamido; alkyl; alkenyl; alkynyl; alkylsilyl; alkoxy groups; aryloxy; alkylthio; alkylsulfinyl; alkylsulfonyl; alkylamino; aralkyl; and heteroaromatic or heteroalicyclic group having from 1 to 3 rings, 3 to 8 ring members in each ring and from 1 to 3N, O or S;

$R^1$ and $R^2$ are each independently hydrogen; hydroxy; substituted or unsubstituted alkanoyl; substituted or unsubstituted alkanoyloxy; substituted or unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms, with at least one of R, $R^1$ and $R^2$ being other than hydrogen;

p is an integer of from 0 to 10; and pharmaceutically acceptable salts thereof, with the exclusion of N-N'-naphthylcarboximide-piperidine, N-N'-naphthylcarboximide-(4phenyl)piperidine; and N-N' (meta-ethylphenyl)carboximide-(4-phenyl)piperidine.

7. A compound having the following formula:

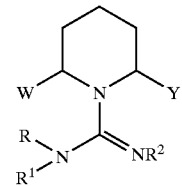

W and Y are each independently substituted or unsubstituted alkyl; substituted or unsubstituted alkenyl; substituted or unsubstituted alkynyl; substituted or unsubstituted alkoxy substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms;

R, $R^1$ and $R^2$ are each independently hydrogen; hydroxy substituted or unsubstituted alkanoyl; substituted or unsubstituted alkanoyloxy, substituted or unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms, with at least one of R, $R^1$ and $R^2$ being other than hydrogen;

and pharmaceutically acceptable salts thereof.

8. A compound of claim 5 that is N-(N'-phenyl) carboximidamide-r-2, c-6-diphenylpiperidine.

9. A compound of claim 3 or 7 wherein W and Y are each independently substituted or unsubstituted alkyl, substituted or unsubstituted carbocyclic aryl or substituted or unsubstituted aralkyl or substituted or unsubstituted heteraromatic.

10. A compound of claim 1, 2, 3, 4, 5, 6, or 7 wherein the X, W and Y groups may be optionally substituted by one or more halogen; cyano; hydroxyl; nitro; azido; alkanoyl; carboxamido; alkyl; alkenyl; alkynyl; alkylsilyl; alkoxy groups; aryloxy; alkylthio; alkylsulfinyl; alkylsulfonyl; alkylamino; carbocyclic aryl; aralkyl; and heteroaromatic or heteroalicyclic group having from 1 to 3 rings, 3 to 8 ring members in each ring and from 1 to 3 N, O or S.

11. A pharmaceutical composition comprising a compound of any one of claims 1 through 8 and a pharmaceutically acceptable carrier.

12. A method of treating a mammal suffering from or susceptible to a neurodegeneration condition, comprising administering to the mammal an effective amount of a compound of the following formula:

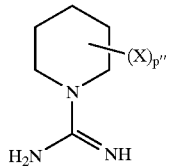

wherein X is independently substituted or unsubstituted alkyl; substituted or unsubstituted alkenyl; substituted or unsubstituted alkynyl; substituted or unsubstituted alkoxy; substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms;

p" is an integer of from 0 to 10; and pharmaceutically acceptable salts thereof.

13. A method of claim 12 wherein the compound is of the following formula:

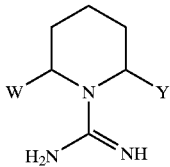

wherein W and Y are each independently substituted or unsubstituted alkyl; substituted or unsubstituted alkenyl; substituted or unsubstituted alkynyl; substituted or unsubstituted alkoxy, substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms; and pharmaceutically acceptable salts thereof.

14. A method of claim 12 wherein the compound is

N-carboximidamide-r-2, c-6-di(4-methylphenyl) piperidine;

N-carboximidamide-r-2, c-6-di(4-isopropylphenyl) piperidine; or

N-carboximidamide-r-2, t-6-di(4-methylphenyl) piperidine;

or a pharmaceutically acceptable salt thereof.

15. A method of claim 13 wherein W and Y are each independently substituted or unsubstituted alkyl, substituted or unsubstituted carbocyclic aryl or substituted or unsubstituted aralkyl or substituted or unsubstituted heteraromatic.

16. A method of claim 12 or 13 wherein the X, W and Y groups may be optionally substituted by one or more halogen; cyano; hydroxyl; nitro; azido; alkanoyl; carboxamido; alkyl; alkenyl; alkynyl; alkylsilyl; alkoxy groups; aryloxy; alkylthio; alkylsulfinyl; alkylsulfonyl; alkylamino; carbocyclic aryl; aralkyl; and heteroaromatic or heteroalicyclic group having from 1 to 3 rings, 3 to 8 ring members in each ring and from 1 to 3 N, O or S.

17. A method of treating a mammal suffering from or susceptible to a neurodegeneration condition, comprising administering to the mammal an effective amount of a compound of the following formula:

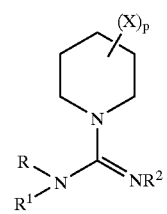

wherein each X is independently substituted or unsubstituted alkyl; substituted or unsubstituted alkenyl; substituted or unsubstituted alkynyl; substituted or unsubstituted alkoxy; substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms;

R is hydrogen; hydroxy; substituted or unsubstituted alkanoyl; substituted or unsubstituted alkanoyloxy; unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms;

$R^1$ and $R^2$ are each independently hydrogen; hydroxy; substituted or unsubstituted alkanoyl; substituted or unsubstituted alkanoyloxy; substituted or unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms, with at least one of R, $R^1$ and $R^2$ being other than hydrogen;

p is an integer of from 0 to 10; and pharmaceutically acceptable salts thereof, with the exclusion of N-N'-naphthylcarboximide-piperidine, N-N'-naphthylcarboximide-(4-phenyl)piperidine; N-N' (meta-ethylphenyl)carboximide-(4-phenyl)piperidine.

18. A method of treating a mammal suffering from or susceptible to a neurodegeneration condition, comprising administering to the mammal an effective amount of a compound of the following formula:

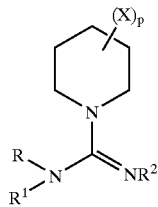

wherein each X is independently substituted or unsubstituted alkyl; substituted or unsubstituted alkenyl; substituted or unsubstituted alkynyl; substituted or unsubstituted alkoxy; substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms;

R is hydrogen; hydroxy; substituted or unsubstituted alkanoyl; substituted or unsubstituted alkanoyloxy; substituted or unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms, wherein substituted R groups may be substituted by one or more halogen; cyano; hydroxyl; nitro; azido; alkanoyl; carboxamido; alkyl; alkenyl; alkynyl; alkylsilyl; alkoxy groups; aryloxy; alkylthio; alkylsulfinyl; alkylsulfonyl; alkylamino; aralkyl; and heteroaromatic or heteroalicyclic group having from 1 to 3 rings, 3 to 8 ring members in each ring and from 1 to 3 N, O or S;

$R^1$ and $R^2$ are each independently hydrogen; hydroxy; substituted or unsubstituted alkanoyl; substituted or unsubstituted alkanoyloxy; substituted or unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms, with at least one of R, $R^1$ and $R^2$ being other than hydrogen;

p is an integer of from 0 to 10; and pharmaceutically acceptable salts thereof, with the exclusion of N-N'-naphthylcarboximide-piperidine, N-N'-naphthylcarboximide-(4-phenyl)piperidine; N-N' (meta-ethylphenyl)carboximide-(4-phenyl)piperidine.

19. A method of treating a mammal suffering from or susceptible to a neurodegeneration condition, comprising administering to the mammal an effective amount of a compound of the following formula:

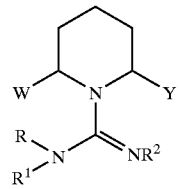

W and Y are each independently substituted or unsubstituted alkyl; substituted or unsubstituted alkenyl; substituted or unsubstituted alkynyl; substituted or unsubstituted alkoxy; substituted or unsubstituted alkylthio; substituted or unsubstituted aminoalkyl; substituted or unsubstituted alkylsulfinyl; substituted or unsubstituted alkylsulfonyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 N, O or S atoms;

R, $R^1$ and $R^2$ are each independently hydrogen; hydroxy; substituted or unsubstituted alkanoyl; substituted or unsubstituted alkanoyloxy; substituted or unsubstituted alkyl; substituted or unsubstituted alkenyl; substituted or unsubstituted alkynyl; substituted or unsubstituted alkoxy; substituted or unsubstituted alkylthio; substituted or unsubstituted alkylamino; substituted or unsubstituted alkylsulfinyl; substituted or unsubstituted alkylsulfonyl; substituted or unsubstituted carbocyclic aryl having at least about 6 ring carbon atoms; or a substituted or unsubstituted heteroaromatic or heteroalicyclic group having from 1 to 3 rings, 3 to 8 ring members in each ring and from 1 to 3 N, O or S atoms, with at least one of R, $R^1$ and $R^2$ being other than hydrogen;

and pharmaceutically acceptable salts thereof.

20. A method of claim 17 wherein the compound is N-(N'-phenyl)carboximidamide-r-2, c-6-diphenylpiperidine.

21. A method of claim 19 wherein W and Y are each independently substituted or unsubstituted alkyl, substituted or unsubstituted carbocyclic aryl or substituted or unsubstituted aralkyl or substituted or unsubstituted heteraromatic.

22. A method of claim 17, 18, or 19 wherein the X, W and Y groups may be optionally substituted by one or more halogen; cyano; hydroxyl; nitro; azido; alkanoyl; carboxamido; alkyl; alkenyl; alkynyl; alkylsilyl; alkoxy groups; aryloxy; alkylthio; alkylsulfinyl; alkylsulfonyl; alkylamino; carbocyclic aryl; aralkyl; and heteroaromatic or heteroalicyclic group having from 1 to 3 rings, 3 to 8 ring members in each ring and from 1 to 3 N, O or S.

23. A method of any one of claims 12 through 15 or 17 through 21 wherein the neurodegeneration condition that the mammal is suffering from is nerve cell death.

24. A method of any one of claim 12 through 15 or 17 through 21 wherein the neurodegeneration condition that the mammal is suffering from is hypoxia, hypoglycemia, brain or spinal cord ischemia, retinal ischemia, brain or spinal cord trauma, heart attack, or stroke.

25. A method of any one of claims 12 through 15 or 17 through 21 wherein the neurodegeneration condition that the mammal is suffering from is a nerve degeneration disease.

26. A method of any one of claims 12 through 15 or 17 through 21 wherein the neurodegeneration condition that the mammal is suffering from is Alzheimer's disease, Amyotrophic Lateral Sclerosis, Down's Syndrome or Korsakoff's disease.

* * * * *